United States Patent [19]

Paegle et al.

[11] 4,232,149
[45] Nov. 4, 1980

[54] 1-(5-FLUORURACIL-1)-2,5-DI-O-ACETYL-β-D-GLUCOFURANURONO-6,3-LACTONE

[76] Inventors: Ruta A. Paegle, ulitsa Fr. Tiesnieka, 2, kv. 2; Marger J. Lidaka, ulitsa Mezhotnes, 37, kv. 1; Regina A. Zhuk, ulitsa Gorkogo, 77, kv. 20; Juris A. Maurinsh, ulitsa Olgas, 3, kv. 7; Aina A. Zidermane, ulitsa Engelsa, 111-a, kv. 9; Marite K. Kilevitsa, ulitsa Dzelzavas, 59, kv. 13, all of Riga, U.S.S.R.

[21] Appl. No.: 928,659

[22] Filed: Jul. 27, 1978

[30] Foreign Application Priority Data

Aug. 2, 1977 [SU] U.S.S.R. .................. 2526564

[51] Int. Cl.³ .................. C07H 17/00; A61K 31/70
[52] U.S. Cl. .................. 536/23; 424/180
[58] Field of Search .................. 536/23; 424/180

[56] References Cited

U.S. PATENT DOCUMENTS

| | | | |
|---|---|---|---|
| 3,155,646 | 11/1964 | Hunter | 536/23 |
| 3,168,513 | 2/1965 | Duschinsky | 536/23 |
| 3,635,946 | 1/1972 | Giller et al. | 536/23 |
| 4,071,680 | 1/1978 | Cook | 536/23 |

FOREIGN PATENT DOCUMENTS 4215112  8/1942  Japan .................. 536/23

Primary Examiner—Johnnie R. Brown
Assistant Examiner—Blondel Hazel
Attorney, Agent, or Firm—Ladas & Parry

[57] ABSTRACT 1-(5-Fluoruacil-1)-2,5-di-O-acetyl-β-D-glucofuranurono-6,3-lactone has the formula

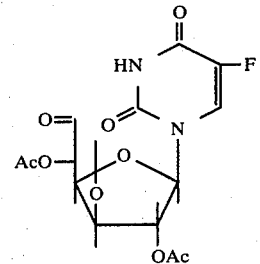

Said substance has a marked antiblastic action. The substance is less toxic compared with the known preparation of similar action.

1 Claim, No Drawings

1-(5-FLUORURACIL-1)-2,5-DI-O-ACETYL-β-D-GLUCOFURANURONO-6,3-LACTONE

FIELD OF THE INVENTION

The invention relates to a novel derivative of 5-fluoruracil, and more particularly it relates to 1-(5-fluoruracil-1)-2,5-di-O-acetyl-β-D-glucofuranurono-6,3-lactone having an antiblastic action.

BACKGROUND OF THE INVENTION

In the prior art there are known a great many chemical compounds having antitumor activity, derivatives of 5-fluoruracil being among them, for example, 1-carbamoyl-5-fluoruracil (Japanese laid-open Application No. 148365/75), 1,3-bis(2-tetrahydropyranyl)-5-fluoruracil (Japanese laid-open Application No. 77072/77), 1-(2-tetrahydrofuryl)-3-cyanoethyl-5-fluoruracil (Japanese laid-open Application No. 77070/77), and 3-acyl-5-fluoruracils (Japanese laid-open Application No. 91880/77).

The most active among the known cytostatics, the derivatives of 5-fluoruracil, are fluorafur-1-(2-tetrahydrofuryl)-5-fluoruracil (U.S. Pat. No. 3,635,946), FUDR, 5-fluoro-2'-desoxyuridine (U.S. Pat. No. 2,949,415) and also FUDA, 5-fluoro-2'-desoxyuridine-5-carboxylic acid (J.Med. Chem. 12, 173, 1969).

A disadvantage of fluorofur is its certain neurotoxicity which, according to reports in the literature, is due to the products of decomposition of the preparation during its metabolism in the living body (S. K. Germane, A. A. Kimenis, Experimental and Clinical Pharmacotherapy, Riga, 1970, issue 1, p. 85–92). As far as FUDR is concerned, its synthesis is complicated and hence expensive, which hinders its wide use in practical medicine. The same applies to FUDA as well, whose synthesis is based on FUDR.

Object of the Invention

The object of the invention is to provide a novel compound having antiblastic properties that would be less toxic and more active compared with the known preparations of similar action.

SUMMARY OF THE INVENTION

According to the present invention, a novel substance is proposed, 1-(5-fluoruracil-1)-2,5-di-O-acetyl-β-D-gluco-furanurono-6,3-lactone having the formula

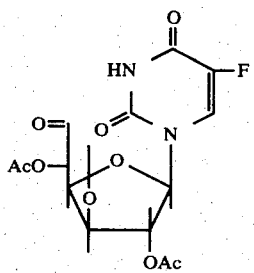

This novel substance will hereinafter be referred to as FUGA.

We have discovered that said substance, FUGA, possesses a marked antiblastic action.

DETAILED DESCRIPTION OF THE INVENTION 1-(5-Fluoruracil-1)-2,5-di-O-acetyl-β-D-glucofuranurono-6,3-lactone (FUGA) is prepared by the interaction of 2,4-bis-(trimethylsilyl)-5-fluoruracil with 1,2,5,-tri-O-acetyl-β-D-glucofuranurono-6,3-lactone in the presence of tin tetrachloride in aprotic solvents.

The reaction is accomplished as follows:

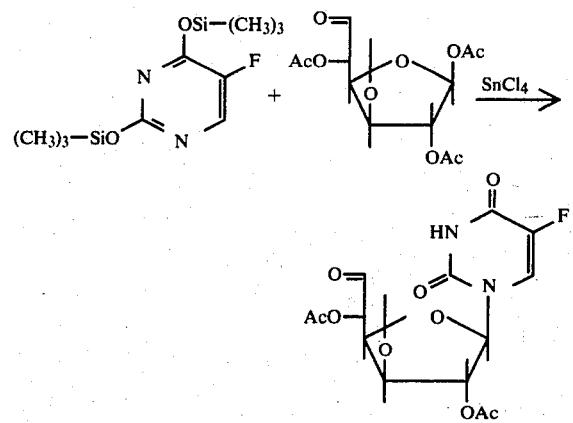

The proposed substance FUGA is a white-crystalline powder, sparingly soluble in water and readily soluble in aprotic solvents. The starting substances, 2,4-bis(-trimethylsilyl)-5-fluoruracil and 1,2,5-tri-O-acetyl-β-D-glucofuranourono-6,3-lactone are readily available known substances.

As has already been said, FUGA has a marked antiblastic action, its toxicity being low.

Compared with the known preparations of similar action, for example a widely used preparation fluorafur, FUGA has a more pronounced antitumor activity toward a wide range of strains of graded tumors of mice and rats, such as leukemia P-388, I-5I78, adenocarcinoma 755, Lewis lung carcinoma, melanoma $B_{16}$, and others. Furthermore, the proposed preparation is several times less toxic than fluorafur, and in addition it is less neurotoxic. Unlike fluorafur, FUGA given in a dose of 20 mg/kg does not practically lower the body temperature, while the former, given in a dose of 115 mg/kg, decreases the body temperature by 3° C. in more than 50 percent animals. Unlike fluorafur, the proposed substance FUGA given in doses to 100 mg/kg intravenously reduces only insignificantly the arterial pressure (by 5–20 mm Hg) in experiments on narcotized cats and dogs, nor does it produce any significant effect on the amplitude and the frequency of respiration. All this indicates that the proposed preparation can be used in oncological practice to provide a sufficiently high effect, its action being free from certain side effects which are otherwise observed in fluorafur therapy. The criterion of the antitumor activity of FUGA is longevity.

The antiblastic action of FUGA was studied in experiments on La hemocytoblastosis and lymphatic leukemia L-1210. La hemocytoblastosis was grafted intraperitoneally to mice of the line $C_{57}Bl/6Y$, in the form of suspended spleen cells in the quantity of 50 mg of the tissue per mouse. Lymphatic leukemia L-1210 was grafted intraperitoneally to mice $BGF_1$ in the quantity of 10⁶ cells of ascites per mouse. The treatment was started in 24 hours. The compounds were suspended in distilled water and given intraperitoneally or orally once a day. The data characterizing the antiblastic action of FUGA are summarized in the Table which follows.

EXAMPLE

To a solution of 15.74 g (0.06 mole) of 2,4-bis(trimethyl-silyl)-5-fluoruracil and 15.1 g (0.05 mole) of 1,2,5-tri-O-acetyl-β-D-glucofuranurono-6,3-lactone in 150 ml of anhydrous methylene chloride is added with stirring 39.15 g (0.15 mole) of tin tetrachloride. The reaction mixture is stirred for two hours and kept at room temperature for 1-2 days after which the mixture is neutralized with sodium bicarbonate solution. The precipitate is separated on a filter and washed with methylene chloride. The organic layer is separated, washed with water to neutral reaction, and dried over sodium sulphate. The solvent is distilled in vacuum, the obtained oily residue is triturated with ether, and filtered. The product is recrystallized from ethyl alcohol. The yield of 1-(5-fluoruracil-1)-2,5-di-O-β-D-glucofuranurono-6,3-lactone is 7.47 g (35.0 percent of theory). The product melts at 138°–140° C.

$(\alpha)_D^{20}$ +109.5 (1.0 MeOH), U-V $\lambda_{max}^{MeOH}$ 267 nm ($\epsilon$ 6620);

TABLE

ANTIBLASTIC ACTION OF 1-(5-FLUORURACIL-1-)-2,5-DI-0-ACETYL--β-D GLUCOFURANURONO-6,3-LACTONE (FUGA) ON La HEMOCYTO-BLASTOSIS AND LYMPHATIC LEUKEMIA L-1210

| No. 1 | Compound 2 | Test-system 3 | Sex of mice 4 | Day of administration 5 | Route of administration 6 | Daily dose, mg/kg 7 | Optimum Daily dose, mg/kg 8 | Maximum extension of life, percent 9 |
|---|---|---|---|---|---|---|---|---|
| 1 | FUGA | La Hemocytoblastosis |  | 1,2 | i/p | 65,108,180,300 | 300 | 148 |
| 2 | FUGA | La Hemocytoblastosis | ♀ | 1,2,3,4,7 | i/p | 108,180,300,500 | 300 | 254 |
| 3 | FUGA | La Hemocytoblastosis | ♂ | 1,2,3,4,7 | i/p | 108,180,300,500 | 300 | 258 |
| 4 | FUGA | La Hemocytoblastosis | ♀ | 1,2,3,4,7 | i/p | 108,300,500,830 | 500 | 75 |
| 5 | FUGA | La Hemocytoblastosis | ♂ | 1,2,3,4,7,8 | p/o | 300,500,833,1380 | 1380 | 40 |
| 6 | FUGA | La Hemocytoblastosis | ♀ | 1,2,3,5,6 | p/o | 2300,3000,3800 | 3000 | 32 |
| 7 | FUGA | L-1210 | ♀ | 1,2,3,4,7 | i/p | 180,300,500,830 | 830 | 77 |
| 8 | FUGA | L-1210 | ♂ | 1,5,9 | i/p | 300,500,830,1383 | 500 | 92 |
| 9 | FUGA | L-1210 | ♀ | 1,5 | i/p | 108,180,300,500 | 500 | 55 |
| 10 | FUGA | L-1210 | ♀ | 1,2,3,4,7 | i/p | 108,180,300,500 | 500 | 54 |
| 11 | FUGA | L-1210 | ♀ | 1,2,3,7 | i/p | 108,180,300,500 | 500 | 83 |
| 12 | FUGA | L-1210 | ♂ | 1,5,9 | i/v | 300,500,830,1383 | 1383 | 82 |
| 13 | FUGA | L-1210 | ♂ | 1,5,9 | i/p | 180,300,500 | 500 | 65 |
| 14 | FUGA | L-1210 | ♂ | 1,5,9 | p/o | 500,830,1383,2292 | 2292 | 78 |
| 15 | FUGA | L-1210 | ♂ | 1,5,9 | p/o | 833,1380,2300 | 1380 | 50 |
| 16 | FUGA | L-1210 | ♀ | 1,2,3,4,7 | p/o | 300,500,833,1380 | 1380 | 32 |
| 17 | Fluorafur | La Hemocytoblastosis | ♂ | 1,2,3,4,7 | i/p | 108,180,300,500 | 180 | 77 |
| 18 | Fluorafur | La Hemocytoblastosis | ♀ | 1,2,3 | i/p | 54–200 | 150 | 130 |
| 19 | Fluorafur | La Hemocytoblastosis | ♀ | 1,2,3,4,7 | i/p | 108,180,300,500 | 180 | 52 |
| 20 | Fluorafur | L-1210 | ♀ | 1,2,3,4,7 | i/p | 65–300 | 300 | 56 |
| 21 | Fluorafur | L-1210 | ♀ | 1 | i/p | 108,180,300,500 | 300 | 49 |
| 22 | Fluorafur | L-1210 | ♀ | 1,5 | i/p | 180,300,500,830 | 500 | 65 |
| 23 | Fluorafur | L-1210 | ♂ | 1,5,9 | i/p | 108,180,300,500 | 500 | 90 |
| 24 | Fluorafur | L-1210 | ♂ | 1,5,9 | p/o | 108,180,300,500 | 500 | 80 |
| 25 | 5-fluorucacil | La Hemocytoblastosis | ♂ | 1 | i/p | 10–150 | 80 | 82 |
| 26 | 5-fluoracil | La Hemocytoblastosis | ♂ | 1,2,3,4,7 | p/o | 108,180,300,500 | 300 | 112 |
| 27 | 5-fluoracil | L-1210 | ♀ | 1,2,3,4,7 | i/p | 38–180 | 39 | 85 |
| 28 | 5-fluoracil | L-1210 | ♀ | 1,2,3,4,7 | i/p | 14–65 | 39 | 129 |
| 29 | 5-fluoracil | L-1210 | ♀ | 1,2,3,4,7 | i/p | 14–65 | 23 | 85 |
| 30 | 5-fluoracil | L-1210 | ♂ | 1,5,9 | i/p | 20–55 | 55 | 116 |

The Table shows that FUGA is a highly active antiblastic compound. In the case with La hemocytoblastosis the life of experimental mice was elongated 258 percent with intraperitoneal administration of the preparation on the 1st, 2nd, 3rd, 4th and 7th day following the leukemia implantation. In the case with lymphatic leukemia L-1210, the life of the mice was elongated 83 percent. The effect of FUGA with oral administration is lower: to 40 percent in the case with La hemocytoblastosis and to 50 percent in the case with lymphatic leukemia L-1210.

For a better understanding of the invention, the following example of preparing 1-(5-fluoruacil-1)-2,5-di-O-acetyl-β-D-glucofuranurono-6,3-lactone (FUGA) is given by way of illustration.

$\nu_{max}^{nujol}$ 1812 cm$^{-1}$ (C=O, γ-lactone); NMR(CDCl$_3$): S 9.7 (IH; NH), 7.26 (IH, I 5.0; HF), 6.09(IH, I 3,0); I'-H), 5.56 (IH, I<0.4; 3'-H), 5.32 (IH, I 3.0; 2'-H), 5.00 (IH, I 3.7; 5'-H) 5.06 (IH, I 4.0 and 3.7; 4'-H), 2.22 (3H, C, COMe), 2.15 (3H, C, COMe).
Found, in percent: C 45.20, H 3.81; N 7.72. C$_{14}$H$_{13}$N$_2$O$_9$F; Calculated, in percent: C 45.43, H 3.5; N 7.5
What is claimed is:
1. 1-(5-Fluoruracil-1)-2,5-di-O-acetyl-β-D-glucofuranurono-6,3-lactone having the formula
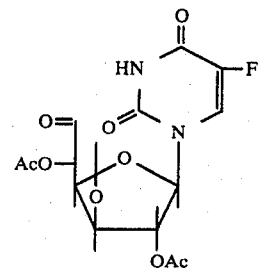
* * * * *